US00PP27180P3

(12) United States Plant Patent
Klemm et al.

(10) Patent No.: US PP27,180 P3
(45) Date of Patent: Sep. 20, 2016

(54) ***CALIBRACHOA* PLANT NAMED 'KLECA13251'**

(50) Latin Name: ***Calibrachoa* sp.**
Varietal Denomination: KLECA13251

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 172 days.

(21) Appl. No.: 14/121,076

(22) Filed: Jul. 28, 2014

(65) Prior Publication Data

US 2016/0029538 P1 Jan. 28, 2016

(51) Int. Cl.
*A01H 5/02* (2006.01)

(52) U.S. Cl.
USPC ..... Plt./413

(58) Field of Classification Search
USPC ..... Plt./413
See application file for complete search history.

*Primary Examiner* — Keith Robinson
(74) *Attorney, Agent, or Firm* — Barbara Campbell; Bethany R. Roahrig; Cochran Freund & Young, LLC

(57) ABSTRACT

A new *Calibrachoa* plant particularly distinguished by having a red-purple flower color and a semi-trailing plant habit, is disclosed.

1 Drawing Sheet

Genus and species: *Calibrachoa* sp.
Variety denomination: 'KLECA13251'.

BACKGROUND OF THE NEW PLANT

The present invention comprises a new and distinct variety of *Calibrachoa*, botanically known as *Calibrachoa* sp., and hereinafter referred to by the variety name 'KLECA13251'. 'KLECA13251' originated from a controlled-cross between the proprietary female *Calibrachoa* variety 'CA-2008-0559' (unpatented) and the proprietary male *Calibrachoa* variety 'CA-2009-1319' (unpatented).

In May 2009, two *Calibrachoa* parental lines, the female variety 'CA-2008-0559' and the male *Calibrachoa* variety 'CA-2009-1319' were crossed via a controlled cross in Stuttgart, Germany and seeds were obtained. The seeds were sown and plants were grown for evaluation. A plant line was selected in May 2010, having red-purple flowers and subsequently named 'KLECA13251'. In May 2010, 'KLECA13251' was first vegetatively propagated by tip cuttings in Stuttgart, Germany. 'KLECA13251' was found to reproduce true to type in successive generations of asexual propagation via tip cuttings.

CROSS REFERENCE TO RELATED APPLICATIONS

Plant Breeder's Rights for 'KLECA13251' were applied for in Switzerland on Jun. 2, 2014, Application No. 14-2955 and in Europe on Jun. 12, 2014 as Application 2014/1604. 'KLECA13251' has not been made publicly available or sold more than one year prior to the filing date of this application.

SUMMARY

The following are the most outstanding and distinguishing characteristics of this new variety when grown under normal horticultural practices in Stuttgart, Germany.

1. Red-purple flower color; and
2. A semi-trailing plant habit.

DESCRIPTION OF THE PHOTOGRAPH

This new *Calibrachoa* plant is illustrated by the accompanying photograph which shows a flowers grown in a pot. The photograph is of a three-month-old plant grown in a controlled greenhouse environment in Stuttgart, Germany in January 2014. The colors shown are as true as can be reasonably obtained by conventional photographic procedures.

DESCRIPTION OF THE NEW VARIETY

The following detailed descriptions set forth the distinctive characteristics of 'KLECA13251'. The data which define these characteristics were collected from asexual reproductions carried out in Stuttgart, Germany. Data was collected on eleven-weeks-old plants grown in Stuttgart, Germany in June 2014. Color references are to The R.H.S. Colour Chart of The Royal Horticultural Society of London (R.H.S.), 5$^{th}$ edition (2007).

Classification:
- *Family*.—Solanaceae.
- *Species*.—*Calibrachoa* sp.
- *Common name*.—*Calibrachoa*.
- *Parentage*.—Female: Proprietary female *Calibrachoa* 'CA-2008-0559' (unpatented). Male: Proprietary male *Calibrachoa* 'CA-2009-1319' (unpatented).

Plant description:
- *Life cycle*.—Annual.
- *Form*.—Semi-trailing.
- *Habit*.—Semi-trailing.
- *Height (from soil line to top of foliage)*.—4.5 cm.
- *Spread*.—29.0 cm.

Propagation: Vegetatively propagated.
- *Type cuttings*.—Tip shoot cuttings.
- *Length of shoot cutting*.—5.5 cm.

*Time to produce a rooted cutting.*—18 days.
*Time it takes to initiate roots.*—4 days at temperatures about 20° C.

Stems:
*Stem color.*—RHS N77 and RHS 144B.
*Pubescence.*—Absent.
*Stem diameter.*—0.2 cm.
*Stem length.*—14.0 cm. From soil line to first node: 1.3 cm. Total length: About 15.5 cm.
*Internode length.*—0.7 cm.

Leaves:
*Arrangement.*—Alternate, simple, sessile.
*Shape.*—Elliptic.
*Apex.*—Obtuse to slightly acute.
*Base.*—Attenuate.
*Margin.*—Entire.
*Surface, both upper and lower.*—Smooth.
*Surface pubescence.*—Absent.
*Venation.*—Pinnate.
*Venation color.*—Upper surface: RHS 144A. Lower surface: RHS 144C.
*Length.*—2.5 cm.
*Width.*—0.8 cm.
*Color.*—Upper surface: RHS 141A. Lower surface: RHS 143A.
*Fragrance.*—Absent.
*Variegation.*—Absent.

Flowers: Single flowers.
*Flowering habit.*—Flower attitude is semi-erect, single, axillary.
*Flower type.*—Determinate inflorescence.
*Flowering requirements.*—A minimum amount of light sun is required.
*Duration of flowers.*—5 days.
*Corolla.*—Smooth texture.
*Conspicuousness of the veins on the upper side of the corolla lobe.*—Weak.
*Shape.*—Trumpet shaped.
*Fragrance.*—Absent.

Flower buds:
*Surface.*—Smooth.
*Length.*—2.0 cm.
*Diameter.*—0.6 cm.
*Shape.*—Irregular to oblong.
*Color.*—RHS 70B.

Peduncle:
*Length.*—0.8 cm.
*Diameter.*—0.1 cm.
*Color.*—RHS 145A.
*Texture.*—Smooth.
*Anthocyanin color.*—RHS N77C.

Flower description:
*Flower depth.*—3.0 cm.
*Flower tube length.*—1.6 cm.
*Flower tube diameter.*—1.3 cm.
*Flower diameter.*—3.7 cm.
*Pedicel color.*—RHS 145A.
*Pedicel.*—Length: 0.8 cm. Diameter: 0.1 cm.
*Calyx.*—Funnel-shaped.

Sepals:
*Shape.*—Lanceolate.
*Apex.*—Acute.
*Margin.*—Entire.
*Base.*—Fused.
*Length.*—1.4 cm.
*Diameter.*—0.4 cm.
*Texture (both sides).*—Smooth.
*Sepal color.*—Upper surface: RHS 144B. Lower surface: RHS 144A.

Petals:
*Shape.*—Heart-shaped.
*Length.*—1.8 cm.
*Apex.*—Obverse.
*Margin.*—Entire, weak undulation.
*Base.*—Open and fused in the tube.
*Pubescence.*—Absent.
*Degree of lobing of the flower.*—Weak.
*Lobe length.*—1.3 cm.
*Lobe width.*—1.8 cm.
*Color.*—Lobe color: Upper surface: RHS 73A. Lower surface: RHS 72C. Corolla tube color: Inner: RHS 14C. Outer: RHS 14D.
*Texture (both sides).*—Smooth.
*Fragrance.*—Absent.

Reproductive organs:
*Stamen number.*—5.
*Stamen color.*—Anther color: RHS 13A. Anther size: 0.8 mm. Anther shape: Ellipsoidal. Filament color: RHS 163D. Filament size: 0.9 mm. Pollen color: RHS 13A. Pollen amount: Scarce.
*Ovary.*—Ovary color: RHS N144C. Placenta arrangement: Ovate. Pistil number: 1. Pistil length: 0.1 cm. Stigma color: RHS 154A. Style length: 0.8 cm. Style color: RHS 149B.

Fruit/seed set: Quantity is small to medium.
Disease/insect resistance: None observed.

COMPARISON WITH PARENTAL LINES AND KNOWN VARIETY

'KLECA13251' is distinguished from its female parent as described in Table 1:

TABLE 1

Comparison with Parental Lines

| Trait | Variety 'KLECA13251' | Female parent 'CA 2008-0559' | Male Parent 'CA-2009-1319' |
|---|---|---|---|
| Flower color | Red-purple | Light blue | Light purple with a red eye |

'KLECA13251' is most similar to the *Calibrachoa* plant named 'KLECA13252' (U.S. application Ser. No. 13/987,413). Differences between the two varieties are described in Table 2:

TABLE 2

Comparison with Similar Variety

| Trait | Variety 'KLECA13251' | Commercial line 'KLECA13252' |
|---|---|---|
| Flower color | RHS 73A | RHS N74A |

We claim:

1. A new and distinct variety of *Calibrachoa* plant named 'KLECA13251' as illustrated and described herein.

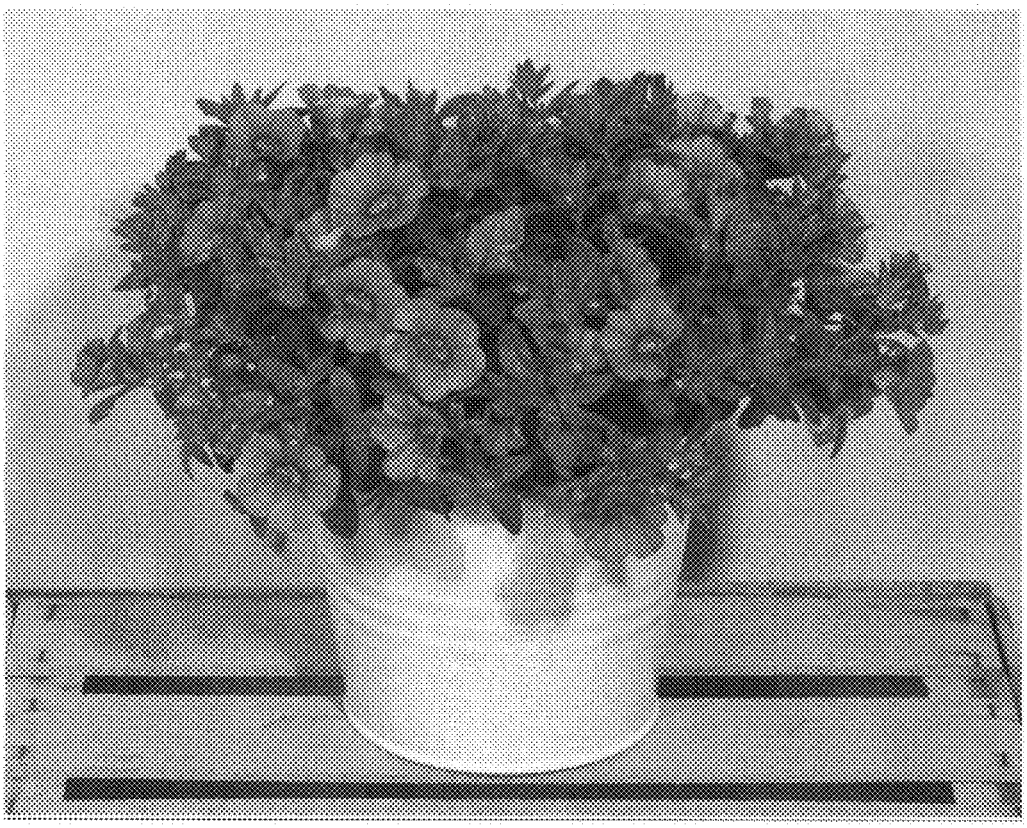

* * * * *